United States Patent [19]

Barrett et al.

[11] Patent Number: 5,196,026
[45] Date of Patent: Mar. 23, 1993

[54] METHOD OF IMPLANTING CORNEAL INLAY LENSES SMALLER THAN THE OPTIC ZONE

[75] Inventors: Graham D. Barrett, Perth, Australia; William J. Link, Irvine; Cary J. Reich, Laguna Hills, both of Calif.

[73] Assignee: Chiron Ophthalmics, Inc., Irvine, Calif.

[21] Appl. No.: 759,599

[22] Filed: Sep. 16, 1991

[51] Int. Cl.⁵ .................................. A61F 2/14
[52] U.S. Cl. ............................................ 623/5
[58] Field of Search ................................ 623/4, 5

[56] References Cited

U.S. PATENT DOCUMENTS

| | | | |
|---|---|---|---|
| 4,607,617 | 8/1986 | Choyce | 623/5 |
| 4,624,669 | 11/1986 | Grendahl | 623/5 |
| 4,655,774 | 4/1987 | Choyce | 623/5 |
| 4,772,283 | 9/1988 | White | 623/5 |
| 4,851,003 | 7/1989 | Lindstrom | 623/5 |
| 4,994,080 | 2/1991 | Shepard | 623/5 |

Primary Examiner—Randy C. Shay
Attorney, Agent, or Firm—Rothwell, Figg, Ernst & Kurz

[57] ABSTRACT

A low or high refractive index corneal inlay optical lens adapted to be inserted between the layers of a cornea to correct refractive errors in eyesight, wherein the implanted lens is of a size or configuration that permits unimpeded passage of nutrients and gases throughout the corneal layers and wherein the composition of the lens relative to that of the surrounding stromal tissue is such that multi-refractive indices may be created and multi-focal corrections are possible.

9 Claims, 2 Drawing Sheets

METHOD OF IMPLANTING CORNEAL INLAY LENSES SMALLER THAN THE OPTIC ZONE

BACKGROUND OF THE INVENTION

1. Field of the Invention

This invention relates to implants designed to be surgically inserted between the layers of the cornea to correct refractive errors. More particularly, the invention relates to corneal implants that can serve as a substitute for conventional spectacles or contact lenses.

2. Description of the Related Art

There have already been proposed artificial lenses for implantation in the eye. Such implants have hitherto been intended, not as corrective lenses, but as a substitute for the natural lens of the eye. For example, when an eye develops a cataract, the natural lens becomes fogged or opaque, thereby impairing vision. When such a cataract is treated, the lens is removed, leaving the eye aphakic. Although it is possible to correct for aphakia using spectacles, the degree of correction requires spectacles so thick as to make them both cumbersome and unattractive. For these reasons, lenses have been designed for correction of aphakia wherein the lens is inserted into the eye during the operation to remove the cataract or at a second operation. Such lenses are of fixed focal length and, as the natural lens has been removed, the eye is no longer capable of accommodation, that is to say, the focal length cannot change to focus at different distances.

It is clear from this description that such previously known implanted lens could never be prescribed as an alternative to conventional spectacles for a person suffering only from myopia or presbyopia.

Another implant that has been used in the past with some success has been the artificial cornea described in U.S. Pat. No. 2,714,712, and generally resembling what is known as a kerato-prosthesis. These implants are designed as a replacement for the natural cornea where the cornea has become fogged or opaque, and are not intended to be a substitute for conventional spectacles or contact lenses.

It is known to resort to surgery in order to correct for defects in eyesight. The various procedures for refractive corneal surgery to correct vision problems such as myopia have not gained general acceptance in ophthalmology. These include radial keratotomy introduced in modern times (1972) by Fyodorov of the USSR, keratomileusis introduced in 1961 by Barraguer of Columbia, keratophakia which uses shaped donor corneas as lens, epikeratophakia which uses an epigraft of homologous tissues, keratotomy to correct astigmatism, and removing clear lens.

Such surgery does not have a fully predictable outcome, and furthermore any non-spherical flattening of the cornea on healing results in an eyesight defect that cannot be corrected by the use of spectacles or contact lenses.

Disks of many different materials have been inserted into corneal stromal pockets, initially to control corneal edema, but more recently to correct refractive errors. Hydrogel and polysulfone lenses have been more successful than other types of lenses so far tried. Use of alloplastic corneal implants would remove the need to rely upon autologous or homologous material in refractive surgery. Corneal implants or inlays are the subject matter of the present invention.

The cornea is a transparent avascular tissue about 10-12 mm in diameter. The cornea functions as a protective membrane and as a "window" through which light rays pass en route to the retina.

The average adult cornea is about 0.65 mm thick at the periphery and about 0.54 mm thick in the center (optic zone). From anterior (front) to the posterior (back), it has 5 distinct layers; the epithelium which is 5 or 6 cell layers thick; a clear acellular Bowman's layer; the stroma (which constitutes about 90% of the thickness of the cornea); the thin Descemet's membrane; and, the single layer endothelium. Sources of nutrition for the cornea are the blood vessels of the limbus, the aqueous humor and tears. The superficial cornea also gets more of its oxygen from the atmosphere.

The zone in the cornea through which incident light passes is known variously as the "optic zone" or "pupillary aperture". The size of the normal pupil varies at different ages and from person to person, but normally is about 3-4 mm—smaller in infancy, tending to be larger in childhood, and again progressively smaller with advancing age.

Previous corneal implants have enjoyed only limited success, in part because of the large diameter of the lenses used and in part because of the composition of such lenses. As will be detailed in the review of the related art below, the opthalmologically more desirable high refractive index lenses previously used prevent access of nutrients and gases such as oxygen to the tissue anterior to the implant and to the corneal tissue posterior to the implant. On the other hand, high water content low refractive index lenses, while reducing or eliminating the problem of nutrient and gas transport, are not able to provide the necessary corrections in refractive error of the eye.

Previous corneal implants have also not been able to provide multifocal refractive correction.

The large diameter of previous corneal implant lenses has also required a less-than-satisfactory surgical approach to implantation. In general, previous corneal inlays have required cutting a large pocket into the cornea and inserting in this pocket the lens which resides predominantly behind Bowman's membrane. With this type of insertion, the large implanted lens distorts the cornea, thereby producing a change in optical power. The disadvantage of such a procedure has been that the distortion is usually in the posterior side of the cornea. Such posterior distortion, however, produces only a very small change in optical power because the difference between the refractive index produced is only the small difference between the inlay/cornea and the aqueous humor.

Choyce, D. P., U.S. Pat. No. 4,607,617, issued Aug. 26, 1986, discloses an implant designed to be inserted between the layers of a cornea of an eye to correct eyesight defects, comprising a polysulfone plastic material of a high refractive index (typically 1.633), of a thickness in the range of 0.1 to 0.4 mm, and capable of being sterilized by steam autoclaving prior to insertion. As the implant is entirely embedded in the cornea, it is said not to be exposed to the atmosphere or to the aqueous humor. The polysulfone material is said to be "relatively permeable to body fluids", although it is not clear that this is so. The lens is inserted by a procedure comprising forming an incision in the outer layer of the cornea, separating layers of the cornea to form a pocket, inserting into this pocket a lens inlay, and resealing the incision. Although this patent neither discloses nor suggests a specific diameter for the lens inlay, reference to FIG. 7b of the specification shows that this diameter is substantially greater than the optic zone of the cornea, which normally is about 3 mm to 4 mm in diameter (Vaughan, D., et al., *General Ophthalmology*, 12th ed., Appleton & Lange, Norwalk, CN, 1989, Ch. 15). See also, Choyce, "Polysulfone Corneal Inlays to Correct Refractive Errors", *Cataract*, 7 (June, 1985). This fact, plus the fact that it is known that high refractive index plastic inlay lenses are poorly permeable to nutrient materials and necessary gases such as oxygen, limits the usefulness of this inlay lens. Further, this corneal inlay does not provide multifocality.

Grendahl, D. T., U.S. Pat. No. 4,624,699, issued Nov. 25, 1986, discloses a corneal inlay for implant made of a plastic material such as polysulfone or PMMA. Recognizing that prior art polysulfone inlay lenses exhibit a property of being poorly permeable to nutrients, fluids and gases, a property of concern to the medical community, the inventor attempts to overcome these disadvantages of the prior art by providing a corneal inlay with a plurality of holes or slots for passage of nutrients through the cornea. The inlay lens is said to have a diameter of approximately 3 mm to 7 mm, preferably of a diameter of 4.5 mm to 6.5 mm, more preferably slightly less than 6 mm in diameter (column 2, lines 21–26). Inlay lenses of such diameter will generally cover the optic zone of an adult cornea, creating the problems of nutrient and gas supply described above. There is no disclosure or suggestion in this patent that the inlay lens could be smaller than the opening of the optic zone, nor is there reference to any property of the lens other than monofocality.

Lindstrom, R. L., U.S. Pat. No. 4,851,003, issued Jul. 25, 1989, discloses corneal inlay lenses applied under the cornea and about the stroma. The lens, which can be made of biocompatible materials such a hydrogel, or synthetic polymers, such as silicone, polysulfone, polycarbonate, cellulose ester or other like materials said to be gas and metabolite permeable, or fenestrated, includes a plurality of fixation holes around a periphery, and a coating on the anterial surface by a material that enhances the growth of corneal epithelial cells into and about said holes, the coating being composed of biological materials such as fibronectin, laminin, a glycosaminoglycan, or a type IV collagen. Although the diameter of the inlay lenses is not specifically disclosed, the dimensions of the holes (up to 1 mm), taken together with FIG. 6 which shows the epicorneal lens implanted below the epithelium, indicates that the diameter of the inlay lens must be substantially greater than the optic zone of the cornea; i.e., about 5 mm to 7 mm. Again, such lenses do not provide a patient with multifocality.

Thus, the prior art inlay lenses are less than satisfactory in important ways. Where large (e.g., 5 mm to 7 mm) hydrogel lenses are used, wherein the water content is high (about 72%) and the index of refraction low (about 1.38), problems of permeability to nutrients and gases are less severe, but the dioptic power is low. Where large polymeric lenses are used, wherein the water content is quite low and the refractive index high (e.g., 1.45 to 1.633), the optic power is satisfactory, but the permeability is poor. Such non-permeability to essential nutrients and gases causes "starvation" in the anterior segments of the stroma, ultimately resulting in extrusion of the inserted lens. Although the permeability problem is reduced by placing holes or slots in polymeric lenses (see Grendahl above), such holes interfere with vision.

Further, none of the prior art inlay lenses provide for multifocality, which is highly desirable in many patients.

There remains, therefore, an important need for intracorneal lenses of a refractive index sufficiently high so as to avoid the need to distort the cornea in order to obtain the desired optical power, of a size sufficiently small so as to simplify surgical insertion, of a size and configuration that permits essential nutrients and gases readily to reach the anterior of the cornea, and of a type that permits either uniforcality of multifocality.

Such an intra-corneal inlay lens has been invented, and it and its use are disclosed below.

SUMMARY OF THE INVENTION

The invention comprises a low or high refractive index corneal inlay lens adapted to be inserted between the layers of the cornea to correct defects in sight, wherein the lens is of a size and configuration that permits nutrients and gases to pass unimpeded from the posterior aspect of the cornea through to the anterior aspect, and wherein the lens is of a composition relative to that of the surrounding tissues such that multi-refractive indices may be created and multi-focal corrections are possible.

In accordance with a first aspect of the invention, there is disclosed a corneal lens of a diameter less than that of the corneal optic zone, wherein the diameter of the lens is such that areas of different refractive indices are created in the optic zone, thereby providing multifocality.

In accordance With a second aspect of the invention, there is disclosed a generally flat annular ring-shaped corneal lens implant of a size and configuration such that no barrier to nutrient passage is present and of a composition such that the lens can provide either unifocality or multifocality.

These and other aspects and objects of the invention will become apparent by reference to the specification below and the appended claims.

DESCRIPTION OF THE DRAWINGS

FIG. 1 is a representation of the anatomic relationship of the inlay lenses of the invention to cornea.

DETAILED DESCRIPTION OF THE INVENTION

The invention comprises corneal implant corrective lenses of novel dimension and configuration, adapted to be surgically inserted into stromal pockets via a very small incision in the corneas of patients suffering from refractive error, the dimensions and configuration of the lenses being such as not to impede the flow of nutrients and gases through the layers of the cornea.

Figure 1B:
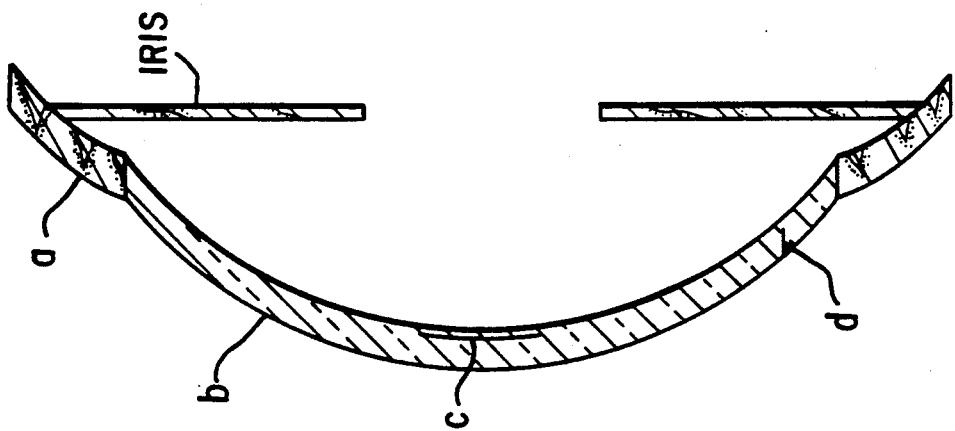
FIGS. 1A and 1B are, respectively, front and side views of the inlaid lens and surrounding anatomical features. Feature a is the sclera, b the cornea, c the location of the inlay of the invention, and d the point of surgical incision.
Figure 1A:
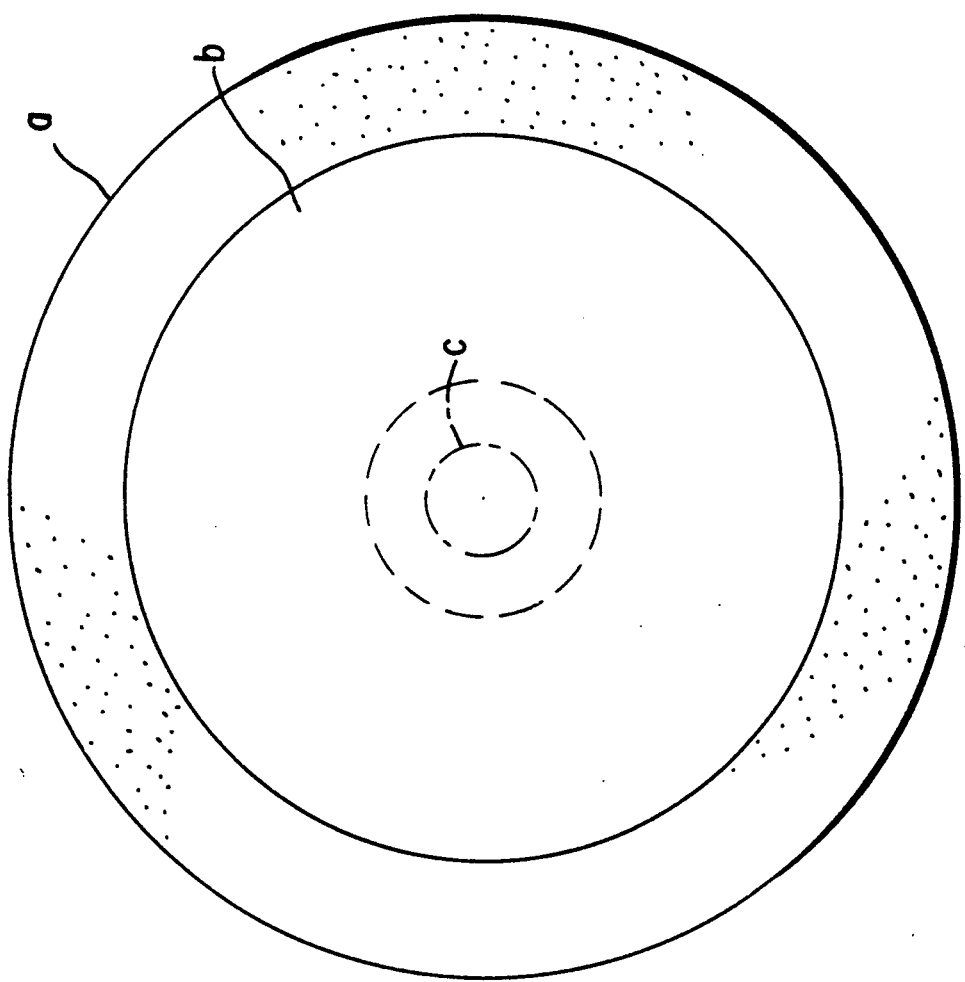
Figure 2:
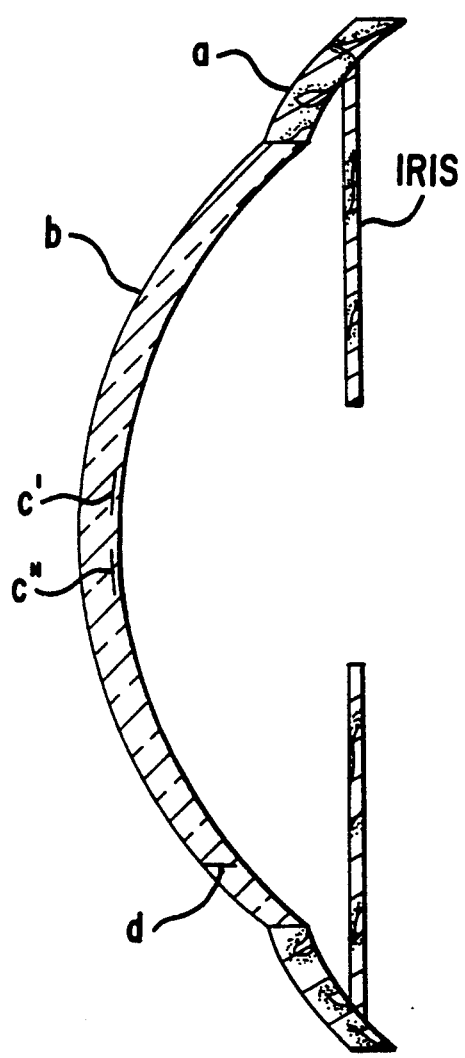
FIG. 2 is a side view similar to FIG. 1A showing two lenses C' and C" implanted in the cornea.

The surgical procedure involves making a stromal cut parallel to the limbus of about 2 mm in length to approximately 75% thickness, using a blunt spatula to make a pocket in the stroma to the center of the corneal optic zone (pupillary aperture), inserting the corrective lens, then resealing the incision (FIG. 1).

It is an important aspect of the invention that the inlay lenses of the embodiments are either of a diameter smaller than that of the optic zone of the cornea or of a configuration so that the implanted lenses, regardless of composition, water content or index of refraction, are designed not to impede the transport of fluids, nutrients and gases to all layers of the cornea.

The invention relates to two embodiments. In one embodiment, the inlay lenses are of a diameter substantially smaller than that of the optic zone of a normal cornea, e.g., about 1 mm to 2 mm. Such lenses create regions of different refractive indices within the optic zone, one created by the lens and the other by the neighboring stroma tissue, thereby providing a useful bifocal capability. The brain is capable of sorting out the different signals and using the information appropriately. This embodiment is not limited to a single small diameter lens; a mosaic of such lenses may be implanted in the same plane, thereby providing for additional multifocality.

In another embodiment, which bears some resemblance to the so-called "bull's eye" intraocular lens, the diameter of the inlay lens may be that of the minimum pupillary aperture, i.e., about 3 mm to about 4 mm, or even larger, but the center of the lens corresponding to the center of the optic zone is drilled out so that the lens resembles an annulus or washer in configuration. The hole in the center of the lens ring permits unimpeded passage of nutrients and gases through the corneal layers. Advantageously, the lens and the adjacent stroma are of different refractive index, thereby providing useful bifocal capability. Thus, for a nearsighted individual, i.e., a myope, the hole in the center of the inlay permits light to image on a portion of the optic zone of the normal cornea, providing for near vision, while light impinging on the peripherally located lens material is refracted, thereby correcting for far vision.

Presbyopes will benefit from the multifocality of the cornea which is generated by its central zone being altered by the small lens of the first embodiment for near vision, while the unaltered peripheral zone remains responsible for distance vision. Myopic patients can benefit in the reverse way by implanting a negative lens in the center, rendering the small central zone optically less powerful.

An enormous number of refractive corrections are possible with the lenses of this invention. Positive and negative lenses of all useful diopters may be employed. The lenses may be of a refractive index greater or less than that of the neighboring corneal tissue. Thus this invention can be applied to presbyopes and myopes, possibly hyperopes and perhaps other corrections as well.

As noted above, the lenses made in accordance with this invention avoid the problems of nutrient and gas passage attendant upon prior art corneal implant lenses. Thus, the invention provides a great deal of flexibility in the selection of lens composition, refractive index and water content. For example, one may use a biocompatible lens of low water content, a diameter of about 2 mm, a center thickness of only about 0.02-0.05 mm, an index of refraction (R.I.) of 1.42 to 1.43, and a power of +2.5 D in the stroma to correct for presbyopia. High water content materials of R.I. slightly greater than or less than the R.I. of the stroma may also be used by an appropriate choice of design. Also suitable are non-water containing biocompatible polymeric material such as the high R.I., relatively rigid polysulfones (e.g., Udel TM, Union Carbide Corp., R.I. typically 1.633) whose high R.I. allows corrections of up to +10 D with a lens 0.04 mm thick, and a correction of −10 D with a, differently shaped lens with a thickness of only 0.01 mm at its center, polyethersulfones (Victrex TM, ICI), polyarylsulfones, Perspex CQ TM or Perspex CQUV (ICI) (R.I. 1.49), polycarbonates, silicones, fluoropolymers, PMMA, cellulose acetate butyrate, or other like materials.

The following examples are merely exemplary of the invention and are in no way intended to limit the scope of the invention which is defined by the specification and the appended claims.

EXAMPLE 1

Insertion of a PMMA Lenticule in the Cornea of Rabbits' Eyes

Physical Parameters:
 Material: PMMA, Meniscus
 Diameter: 2.0 mm; edge thickness: 0.02 mm; center thickness: 0.022 mm; Base curve: 7.6 mm; power: +2.5D.
Sterilization: gamma radiation 2.5-3 Mrad due to the thinness of the lenticule, the slight yellowing of the PMMA is negligible.

Implant Procedure

1.1 Surgical Procedure

Perform a 2 mm incision approximately 75% of the stromal thickness about 1 mm central from the limbus in clear cornea. Using a blunt spatula, make a pocket to the center of the cornea.

1.2 Intraoperative Drug Treatment

The resulting wound is then rinsed with irrigating solution.

1.3 Lens Placement

Prior to placing the lens, several drops of irrigating solution are placed on the eye. The appropriate lens is poured into a wire strainer and rinsed with sterile saline. Several drops of irrigating solution are placed on the lens. The lens is carefully picked up with a non-toothed forceps and inserted in the pocket. The lens is then moved to the center of the cornea. Care must be taken to ensure that the lens is well centered.

1.4 Completion

Flush the eye well with irrigating solution. Suture if necessary. Apply two (2) drops of postoperative drug solution.

1.5 Postoperative Treatment

Give Maxidex 2X daily (weekend treatment is once daily), and antibiotics as necessary.

EXAMPLE 2

Insertion of a Hydrogel Lenticule in the Cornea of Rabbits' Eyes

Physical Parameters:
 Material: Hefilcon A; Meniscus
 Water content: 45%; Refractive Index; 1.425

Diameter: 2.0 mm; edge thickness: 0.02 mm; center thickness: 0.023 mm; Base curve: 7.6 mm; power: +2.5D.

Sterilization method: Autoclaving

Implant Procedure

2.1 Surgical Procedure

Perform a 2 mm incision approximately 75% of the stromal thickness about 1 mm central from the limbus in clear cornea. Using a blunt spatula, make a pocket to the center of the cornea.

2.2 Intraoperative Drug Treatment

The resulting wound is then rinsed with irrigating solution.

2.3 Lens Placement

Prior to placing the lens, several drops of irrigating solution are placed on the eye. The appropriate lens is poured into a wire strainer and rinsed with sterile saline. Several drops of irrigating solution are placed on the lens. The lens is carefully picked up with a non-toothed forceps and inserted in the pocket. The lens is then moved to the center of the cornea. Care must be taken to ensure that the lens is well centered.

2.4 Completion

Flush the eye well with irrigating solution. Suture if necessary. Apply two (2) drops of postoperative drug solution.

2.5 Postoperative Treatment

Give Maxidex 2× daily (weekend treatment is once daily), and antibiotics as necessary.

EXAMPLE 3

Insertion of a Hydrogel Lenticle in the Cornea of Cats' Eyes

Physical Parameters:
  Material: Hefilcon A; Biconvex
  Water content: 45%, Refractive Index: 1.425
  Diameter: 2.0 mm; edge thickness: 0.02 mm; center thickness: 0.04 mm; Anterior radius: 7.0 mm; Posterior radius: 9.8 mm; Power: +2.5D.

Sterilization method: Autoclaving

Implant Procedure

3.1 Surgical Procedure

Perform a 2mm incision approximately 90% of the stromal thickness about 1 mm central from the limbus in clear cornea. Using a blunt spatula, make a pocket to the center of the cornea.

3.2 Intraoperative Drug Treatment

The resulting wound is then rinsed with irrigating solution.

3.3 Lens Placement

Prior to placing the lens, several drops of irrigating solution are placed on the eye. The appropriate lens is poured into a wire strainer and rinsed with sterile saline. Several drops of irrigating solution are placed on the lens. The lens is carefully picked up with a non-toothed forceps and inserted in the pocket. The lens is then moved to the center of the cornea. Care must be taken to ensure that the lens is well centered.

3.4 Completion

Flush the eye well with irrigating solution. Suture if necessary. Apply two (2) drops of postoperative drug solution.

3.5 Postoperative Treatment

Give Maxidex 2× daily (weekend treatment is once daily), and antibiotics as necessary.

We claim:

1. A method of treating refractive errors in a patient comprising the steps of:
   a) making a stromal cut in a cornea parallel to the limbus;
   b) forming a pocket in said stromal cut to the center or close to the center of said cornea;
   c) inserting in said pocket one or more solid optical lenses having no apertures therethrough composed of a biocompatible-hydrogel, polymeric material, cellulose ester, or silicone of a diameter or configuration such that the entire optic zone of said cornea is not covered by said lens or lenses, wherein the diameter of said lens is substantially less than the diameter of said optic zone, thereby producing a cornea with multiple refractive indices and multiple focalities created only by the presence or absence of said lens or lenses such that the focal distance created in one or more portions of the cornea is suitable for distance vision and the focal distance created in one or more other portions of the cornea is suitable for near vision; and
   d) allowing the incision to heal with or without sutures or other means of closing the incision.

2. A method of claim 1, wherein said stromal cut is made to be about 2 mm to about 3 mm in length and extends to between about 50% to about 95% of the stromal thickness.

3. A method of claim 1, including selecting said lens or lenses to have a diameter between about 1.0 mm and about 3.0 mm.

4. A method of claim 1 wherein said composition of said lens or lenses is a polymeric material selected from the group consisting of a polysulfone, a polyethersulfone, a polyarylsulfone, a polycarbonate, a fluoropolymer, and a polymethyl methacrylate.

5. A method of claim 1, wherein two or more of said lenses are implanted in said corneal optic zone.

6. A method of claim 1, wherein said lens or lenses are selected to have a positive diopter.

7. A method of claim 1, wherein said lens or lenses are selected to have a negative diopter.

8. A method of claim 1, wherein said lens or lenses are selected to have a refractive index greater or less than that of the surrounding stromal tissue.

9. A method of claim 1, wherein the refractive error to be corrected is selected from the group consisting of myopia, presbyopia, and hyperopia.

* * * * *